United States Patent [19]
Rosen

[11] Patent Number: 5,876,960
[45] Date of Patent: Mar. 2, 1999

[54] BACTERIAL SPORE DETECTION AND QUANTIFICATION METHODS

[75] Inventor: David L. Rosen, Silver Spring, Md.

[73] Assignee: The United States of America as represented by the Secretary of the Army, Washington, D.C.

[21] Appl. No.: 914,020

[22] Filed: Aug. 11, 1997

[51] Int. Cl.$^6$ .............................. C12Q 1/04; C12Q 1/06; C12Q 1/00

[52] U.S. Cl. .................................. 435/39; 435/4; 435/34; 435/40.5; 435/40.51; 435/242; 435/968

[58] Field of Search ................................. 435/4, 34, 39, 435/40.5, 40.51, 242, 968

[56] References Cited

U.S. PATENT DOCUMENTS

| | | | |
|---|---|---|---|
| 4,058,732 | 11/1977 | Wieder | 250/461 |
| 4,150,295 | 4/1979 | Wieder | 250/458 |
| 4,374,120 | 2/1983 | Soini et al. | 436/546 |
| 4,572,803 | 2/1986 | Yamazoe et al. | 534/16 |
| 4,978,625 | 12/1990 | Wagner et al. | 436/518 |
| 5,186,946 | 2/1993 | Vallieres | 424/613 |
| 5,190,865 | 3/1993 | Schultz | 435/108 |
| 5,298,409 | 3/1994 | Schultz | 435/106 |
| 5,308,754 | 5/1994 | Kankare et al. | 435/7.4 |

OTHER PUBLICATIONS

Johnen et al. Soil Biol. Biochem. vol. 10, pp. 487–494, 1978.
Lewis, J.C. Anal. Biochem. vol. 19, pp. 327–337, 1967.
*Bacterial Spore Detection and Determination by Use of Terbium Dipicolinate Photoluminescence*, David L. Rosen et al., Analytical Chemistry, vol. 69, No. 6, pp. 1082–1085, Mar. 15, 1997.
*Bacterial Spore Detection and Determination by Use of Terbium Dipicolinate Photoluminescence Abstract*, David L. Rosen et al., Analytical Chemistry, vol. 69, pp. 1082–1085, Mar. 1, 1997.
*Spectroscopic Studies of TB Complexes*, Inorganic Chemistry, vol. 20, No. 8, 1981, pp. 2616–2617 (the article shows diagrams of dipicolinic acid and lanthanide dipicolinate).
*A Simple, One–Step Fluorometric Method for Determination of Nanomolar Concentrations of Terbium* Thomas D. Barela and A. Dean Sherry, Analytical Biochemistry 71, 351–357 (1976).

Primary Examiner—Leon B. Lankford, Jr.
Assistant Examiner—Christopher R. Tate
Attorney, Agent, or Firm—Paul S. Clohan; U. John Biffoni

[57] ABSTRACT

The invented methods are effective for the detection and quantification of bacterial spores in a sample medium. A lanthanide such as europium or terbium is combined with a medium to be tested for endospore content. The lanthanide will react with calcium dipicolinate present in any bacterial spores in the sample medium to produce a lanthanide chelate, specifically, terbium or europium dipicolinate. The lanthanide chelate has distinctive absorbance and emission spectrums that can be detected using photoluminescence testing, for example. The occurrence of emission from the sample medium upon excitation at wavelengths distinctive of the lanthanide chelate thus reveals the presence of spores in the sample medium. The concentration of spores can be determined by preparing a calibration curve that relates absorbance or emission intensities to spore concentrations for test samples with known spore concentrations. The calibration curve can be used to determine the spore concentration of a sample medium using the absorbance or emission intensity for the combined lanthanide-sample medium.

43 Claims, 5 Drawing Sheets

BACTERIAL SPORE DETECTION AND QUANTIFICATION METHODS

STATEMENT OF GOVERNMENT RIGHTS IN THE INVENTION

The invention described herein has been assigned in its entirety to the U.S. Government as represented by the U.S. Army. Accordingly, the U.S. Government owns all exclusive rights in the invention.

BACKGROUND OF THE INVENTION

1. Field of the Invention

This invention is directed to a method for detecting the presence and concentration of bacterial spores in a medium.

2. Description of the Related Art

The detection of bacterial spores, sometimes called 'endospores', is useful for a wide variety of purposes. For example, in military applications, biological warfare agents include spore-producing bacteria that cause diseases such as anthrax, botulism, gas gangrene and tetanus. Because spore-producing bacteria are relatively uncommon in certain environments such as in ambient air, the detection of spores can be used to sense the release of such agents. The detection of spores of such bacteria can also be important in determining and implementing appropriate countermeasures against such agents. In agricultural technologies, spore-producing bacteria such as *Bacillus thuringiensis* are often used as insecticides. Spores in soil or plant samples can be monitored to ensure that the bacteria population is sufficiently high to be effective against insect pests. In the sanitation and hygiene fields, the detection of bacteria spores can be useful to monitor indoor environments, water quality, and food quality. In addition, the detection of nonviable bacterial spores can be useful to paleontologists.

Bacterial endospore concentrations are not easily determined with conventional techniques. Among the primary conventional techniques are microscopy and plate culture counting, both of which are extremely slow and tedious to perform. It would be highly desirable to provide methods that allow rapid and simplified detection and determination of the concentration of bacterial endospores.

SUMMARY OF THE INVENTION

This invention overcomes the above-noted disadvantages. An endospore detection method in accordance with this invention detects the presence of bacterial endospores in a sample medium. Broadly stated, the detection method includes steps of combining a lanthanide with a sample medium, and determining whether the combined lanthanide and sample medium includes a lanthanide chelate indicative of the presence of bacterial endospores. The determination step is preferably performed using photoluminescence testing that reveals the presence of any lanthanide chelate that may have formed upon combining the lanthanide and medium. Because certain chelate-forming molecules, such as dipicolinate anions, are relatively rare in nature, except in bacterial endospores and a few other biological systems, the method is a strong indicator of the presence of endospores in the sample medium.

In a preferred embodiment of the detection method, the sample medium can be prepared with a buffer solution in which is placed a sample that is to be tested for endospore content. The detection method includes a step of combining a lanthanide such as terbium or europium, with the sample medium. The lanthanide reacts with dipicolinate in the bacterial endospores if present in the medium to form a lanthanide chelate dissolved in the medium. More specifically, the lanthanide reacts with calcium dipicolinate that is naturally present in the endospore, and relatively uncommon in nature. The lanthanide replaces the calcium to form a lanthanide chelate.

In the preferred embodiment of the detection method, photoluminescence testing is performed by exciting any lanthanide chelate formed in the step of combining the lanthanide with the medium. A preferred excitation technique uses intense light from a laser or lamp directed to the medium, that operates at excitation wavelengths that will produce emission at the lanthanide chelate's distinctive emission wavelengths. The preferred photoluminescence testing also includes a step of sensing whether emission occurs at a distinctive emission wavelength of the lanthanide chelate as a result of the excitation step. The lanthanide chelate has a long-lived luminescence with a distinctive emission spectrum that has sharp emission peaks at wavelengths that are not significantly present in ambient environments. The lanthanide chelate also has a relatively large Stokes' shift. Thus, the emission peaks occur at wavelengths that are relatively distant from the excitation energy wavelength. Accordingly, emission wavelengths can be readily distinguished from excitation wavelengths in photoluminescence testing of the lanthanide chelate. The sensing step can be performed over selected wavelengths greater than the excitation wavelength(s) through long-pass optical filtering. The lanthanide chelate has a relatively long luminescence lifetime that can be used to discriminate it from concomittants. The sensing step can be performed with a photodetector such as a photomultiplier or other optical detection device, that generates an electric signal indicative of the emission intensity. Alternatively, although less preferred, photoluminescence testing of the combined lanthanide-sample medium can be performed by determining whether the absorption spectrum of the combined lanthanide-sample medium occurs at wavelengths distinctive of the lanthanide chelate, to determine whether endospores are present in the sample medium.

To aid in the step of determining whether bacterial endospores are present in the medium, the detection method can include a step of determining a threshold emission intensity level above which it is known that the sample medium contains at least some endospore content. The threshold level can be established by exciting a blank medium that contains no lanthanide chelate. For example, the sample medium or the lanthanide in solution can be used as the blank medium. The emission intensity at the distinctive emission wavelength that is selected for use in determining whether the lanthanide chelate is present, is determined for the blank medium through photoluminescence testing and used as a threshold level. The threshold level can also be set to an output level of the spectrofluorometer's detection element under a condition in which the detection element is shielded from light. If under photoluminescence testing the combined lanthanide-sample medium produces an emission intensity above the threshold level, the sample medium is determined to have at least some bacterial endospore content. Conversely, if the emission intensity of the combined lanthanide-sample medium is relatively close to the threshold level, the sample medium is determined to contain no significant endospore content. Also, in the method, the combined lanthanide and sample medium can be filtered to separate soluble and insoluble portions of the sample medium before the excitation and emission detection steps. The filtering step sharpens but reduces the magnitude of peak emissions of the lanthanide chelate relative to the unfiltered sample medium.

A quantification invented method is useful for determining the concentration of bacterial endospores in a sample medium. The quantification method generally includes steps of combining a lanthanide with a sample medium, and determining the concentration of bacterial endospores present in the combined lanthanide and sample medium, based on the amount of lanthanide chelate resulting from the combination of lanthanide with the sample medium. The endospore concentration is preferably determined by detecting the emission intensity generated by the lanthanide chelate in the performance of photoluminescence testing.

Similarly to the detection method, the determination of bacterial endospore concentration can be performed using photoluminescence. Thus, the quantification method can include a step of exciting any lanthanide chelate formed in the combining step with an excitation energy distinctive of the lanthanide chelate, and determining the emission intensity that results from the excitation step at an emission wavelength distinctive of the lanthanide chelate. The quantification method can also include a step of determining concentration of bacterial endospores present in the medium, based on the emission intensity determined in the sensing step. The determination of the endospore concentration can be performed by preparing two or more test media with predetermined different concentrations of bacterial endospores. The test is media are excited and their emission intensities noted under conditions that are the same as those actually used to test the sample medium with unknown endospore content. The emission intensities are used to establish a calibration curve that relates emission intensity at the distinctive emission wavelength to the concentration of bacterial endospores. The emission intensity for the medium with an unknown bacterial spore concentration can be related to its actual spore concentration using the calibration curve. Also, as previously described with respect to the detection method, threshold levels can be determined from a blank medium such as the lanthanide in solution or the sample medium before combination, to establish threshold levels corresponding to the limit of detection of endospore concentration. Any emission above the threshold level is indicative of the presence of lanthanide chelate, and hence also of bacterial endospore content. Alternatively, rather than using the emission spectra of the media, photoluminescence testing can be performed using the distinctive absorption spectra of the lanthanide chelate.

These together with other features and advantages, which will become subsequently apparent, reside in the details of construction and operation as more fully hereinafter described and claimed, reference being made to the accompanying drawings, forming a part hereof, wherein like numerals refer to like parts throughout the several views.

DESCRIPTION OF THE PREFERRED EMBODIMENTS

Figure 1:
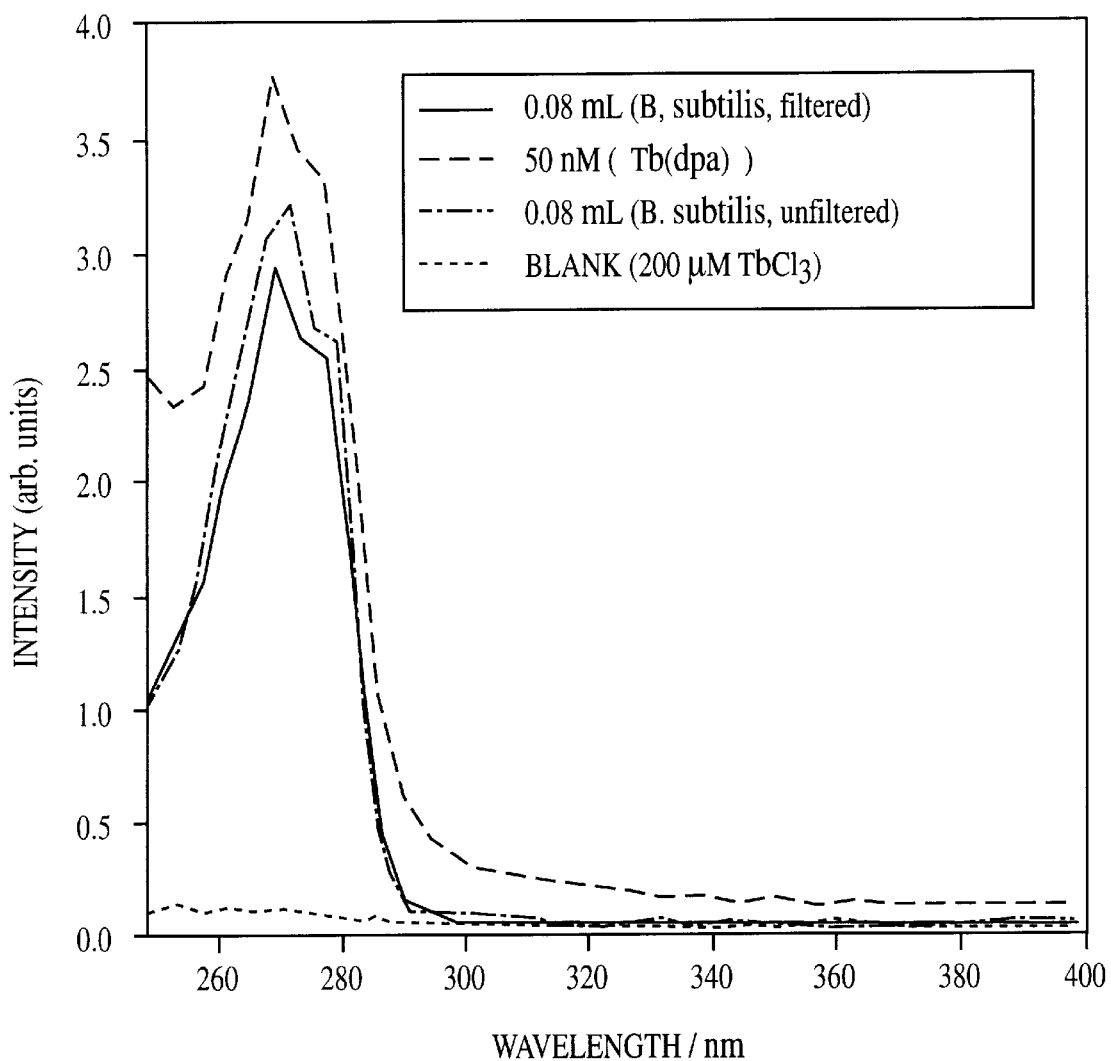
FIG. 1 is a graph of absorbance intensity versus wavelength for solutions of 50 nanomolar (nM) terbium dipicolinate, 0.08 milliliters (mL) filtered and unfiltered *Bacillus subtilis* sample media, and a blank medium containing 200 $\mu$M of terbium chloride.

The initial preparation steps are similar for both the detection and quantification methods of this invention. A sample medium can be prepared by placing a sample that is desired to be tested for endospore content into a buffer solution to form a suspension. For example, the buffer solution can be a TRIS or acetic buffer solution that are commercially available from Aldrich Chemical Co. of Milwaukee, Wis.

The lanthanide is preferably prepared in solution form for use in the invented methods. The lanthanide solution can be prepared by serial dilution by combining terbium or europium chloride, bromide, iodide, or other anion with a buffer solution such as the TRIS buffer or acetic buffer. At relatively high concentrations (>1 mM), the lanthanide can precipitate out of the solution after several hours. Precipitation can be avoided at the relatively low concentrations (e.g., <300 $\mu$M) that are preferred in the invented methods.

In both the detection and quantification methods, the lanthanide solution is combined with the sample medium. If bacterial endospores are present in the sample medium, the lanthanide (e.g. terbium or europium) reacts with calcium dipicolinate in the endospore to produce a lanthanide chelate, specifically, terbium or europium dipicolinate. The reaction that occurs is believed to be:

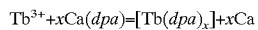

$$Tb^{3+}+xCa(dpa)=[Tb(dpa)_x]+xCa$$

where x is a positive integer that is not indicated, as the stoichiometry of the reaction is not known at this time. The resulting lanthanide chelate is dissolved in solution. The terbium or europium dipicolinate have a distinctive photoluminescence absorption and emission spectra that can be used to indicate the presence of the endospores.

Optionally, in both the detection and quantification methods, the sample medium can be filtered to separate solubles from insolubles including any endospores that may be present in the sample medium. Filtration can be performed with a Millipore Millex-GV syringe filter with a pore size less than the diameter of the endospores that are desired to be detected. For example, a 0.22 $\mu$m pore size is effective for most endospore-producing bacteria are typically more than 1 $\mu$m in diameter. The resulting filtered sample medium can be used for determination of endospore presence in the sample.

To detect the presence of any lanthanide chelate, and hence also the presence of endospores in the sample, in the detection and quantification methods, the combined lanthanide and sample medium are preferably subjected to photoluminescence testing. More specifically, the combined lanthanide-sample medium are excited with energy within the excitation spectra, preferably at the absorbance peaks, of the lanthanide chelate. In the preferred embodiment, the excitation energy is supplied with relatively intense light, such as that generated by a laser or a lamp (an ultraviolet lamp, for example), that is directed to the filtered or unfiltered sample medium. For terbium dipicolinate, the preferred excitation energy is in the wavelength ranges of 270±5 nanometers (nm) and/or 278±5 nm. During or shortly after excitation to allow background luminescence to decay, the emission intensity at a wavelength distinctive of the lanthanide chelate is detected. Such distinctive emission wavelengths for terbium dipicolinate include emission peaks at ranges of 490±10 nm, 546±10 nm, 586±10 nm and 622±10 nm. As is well-known in spectrofluoroscopy, the emission intensity detection can be performed with a photodetector such as a photomultiplier or other optical detection device that produces an electric signal indicative of emission intensity from the sample medium. Preferably, a filter is positioned in front of the detector element and used to reject light at relatively low wavelengths. For example, a 420 nm long-pass filter can be used to eliminate light that is not of interest such as signal that is caused by second-order diffraction of elastically scattered excitation light. The excitation spectra can be generated, and the resulting emission spectra detected, using commercially available spectrofluorometers such as the SLM Model 48000S spectrofluorometer produced by Spectronics Instruments of Rochester, N.Y. In the detection method, if the emission intensity at wavelengths distinctive of the lanthanide chelate is significantly above a threshold level, endospore content is determined to be present in the sample medium. On the other hand, if the emission intensity at the lanthanide chelate's distinctive emission wavelength(s) is relatively low, for example, close to the threshold level, the lanthanide chelate, and hence bacterial endospores, are determined not to be significantly present in the sample medium. The threshold level used to determine the presence of endospores can be established as the emission intensity under a condition in which the fluorometer's emission detection element is shielded from light. Alternatively, before combining the lanthanide with the sample medium, the threshold level can be determined using the photoluminescence emission intensity from the lanthanide solution or sample medium at the same excitation and absorbance or emission wavelengths as used to test the lanthanide-treated sample medium.

Rather than sensing whether luminescence occurs at selected wavelengths distinctive of the lanthanide chelate, the presence of luminescence after a predetermined time delay from the end of an excitation pulse can also be used to determine whether a sample medium treated with lanthanide contains any significant bacterial endospore content. This technique is sometimes referred to as a 'time-resolved' detection technique. More specifically, an energy pulse from a laser or lamp, for example, can be applied at an energy that will excite any lanthanide chelate present in the lanthanide-treated sample medium. After a short delay from the end of the excitation pulse, a photodetector can be used to determine whether any luminescence exists that is indicative of the presence of lanthanide chelate, and hence endospores. Because most substances have luminescence lifetimes on the order of nanoseconds whereas lanthanide chelates such as terbium dipicolinate and europium dipicolinate have relatively long luminescence lifetimes (2.0 milliseconds and 0.8 milliseconds, respectively), the presence of any luminescence after several nanoseconds is highly indicative of the presence of the lanthanide chelate and thus also endospores. On the other hand, if no significant luminescence is present after several nanoseconds, the sample medium is determined to contain no significant endospore content.

In many respects, the endospore quantification method is similar to the detection method described above. However, rather than comparing the photoluminescence emission intensity of the sample medium with a threshold level, the quantification method uses a calibration curve from which the bacterial spore concentration can be determined from the emission intensity detected for the sample medium. The calibration curve is determined in the quantification method in the following manner. Two or more test sample media are prepared using the same solution as used for the sample medium containing an unknown concentration of endospores. Lanthanide is combined with the test sample media in the same molarity as used to prepare the lanthanide-sample medium with the unknown endospore concentration. The test sample media are subjected to photoluminescence testing by excitation and absorption or emission detection at the same wavelengths used for the lanthanide-sample medium with the unknown concentration of endospores. Alternatively, if a time-resolved luminescence detection technique is used, detection is performed using the same excitation energy and time-delay as that used with the sample medium containing the unknown content of endospores. The emission intensities determined for the test media can be used to plot the calibration curve that functionally relates the emission intensity to known spore concentrations. Therefore, by interpolation or extrapolation between the emission intensities of the sample media with known endospore concentration, the emission intensity for the sample medium with unknown concentration can be used with the calibration curve to determine its endospore concentration.

EXAMPLE 1

The following example illustrates the effectiveness of the invented endospore detection and quantification methods.

Sample media of both endospore suspensions with terbium chloride and terbium dipicolinate were prepared for comparison. The sample media were prepared with a 50 mM TRIS buffer solution which included 6.36 g/L of Trizma-HCl, 1.16 g/L of Trizma base, and 4% (v/v) ethanol with a pH of 7.7. The terbium chloride was prepared in solution by serial dilution. The terbium dipicolinate [$Tb(dpa)_x$] solution was prepared by adding $H_2dpa$ solution to 41 $\mu$M of terbium chloride ($TbCl_3$).

A stock spore suspension of *Bacillus subtilis* was obtained from AMSCO sterility products of Apex, North Carolina. The mean population recovery (i.e., concentration of spores in colony forming units per milliliter) of the suspension was $6.2\times10^9$ CFU/mL in 40% (v/v) ethanol.

Referring to FIG. 1, the absorbance intensities for excitation of a 50 nM terbium dipicolinate solution, a sample medium containing a 0.08 mL volume of endospore stock suspension combined with 10 mL of 200 $\mu$M terbium chloride both before and after filtration with a syringe containing 0.22 $\mu$m pore-size filters, and a 200 $\mu$M terbium chloride solution, were examined in a wavelength range from 250–400 nm using a Perkin-Elmer Model Lambda 6 UV-vis spectrophotometer with 4 nm resolution. The absorbance intensities are normalized by division with the excitation intensity throughout the Figures. The terbium dipicolinate solution exhibits expected absorbance of excitation energy at its distinctive peaks, specifically, at about 270 and 278 nm. Both the filtered and unfiltered sample media with the combined endospore-terbium chloride exhibit absorbance spectra that mirrors that of the terbium dipicolinate solution, demonstrating that terbium reacted with calcium dipicolinate in the endospores to produce terbium dipicolinate. The filtered sample media exhibits a narrower bandwidth and lower peak compared with the unfiltered sample. This phenomenon is believed to occur because of the relatively large amount of insoluble bacterial particles present in the unfiltered sample. The blank sample medium of terbium chloride solution demonstrates low absorbance over the wavelength range from 250–400 nm.

The absorbance spectra of FIG. 1 can be used to determine the presence of terbium dipicolinate, and hence bacterial endospores, in the two terbium-endospore sample media. More specifically, if a sample media contains significant endospore content excited at a wavelength in the range from 260 to 290 nm, the sample media will exhibit at least some absorbance over the threshold level established by the blank sample medium. Conversely, if the sample medium exhibits no significant emission above the threshold level, it can be concluded that the sample medium contains no significant endospore content. Further, the absorbance intensity is proportional to the concentration of endospores in the sample media, and can be used to determine the endospore concentration with a calibration curve. However, the use of the absorbance spectra is not preferred for practice of the invented methods because the lanthanide chelate generally has a relatively small absorbance measurable only at relatively high concentrations.

Figure 2:
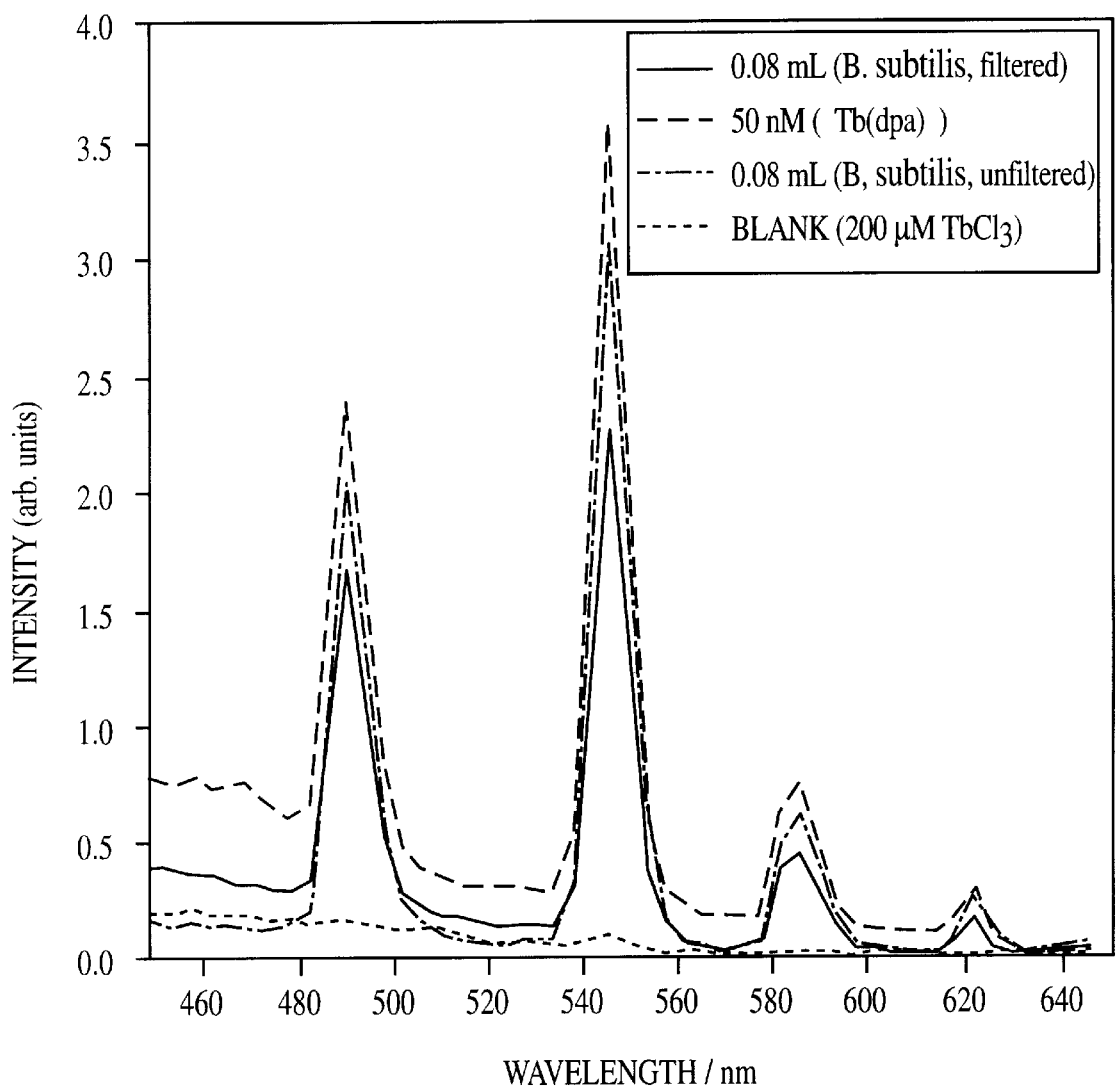
FIG. 2 is a graph of emission intensity versus wavelength for solutions of 50 nM terbium dipicolinate, 0.08 mL filtered an unfiltered *Bacillus subtilis* sample media, and a blank containing 200 $\mu$M of terbium chloride.

FIG. 2 shows the emission intensities for the same sample media and solutions described in FIG. 1 under an excitation wavelength of 270 nm. As expected, the emission intensities of the filtered and unfiltered sample media closely follow the emission spectrum for the terbium dipicolinate. The filtered sample has a narrower bandwidth at its peak emission intensities of 490 nm, 546 nm, 586 nm and 622 nm than the unfiltered sample, and is smaller in magnitude at its peak intensities relative to the unfiltered sample, which is believed to be caused by the relatively large amount of insoluble bacterial particles present in the unfiltered sample medium compared to the filtered medium. As expected, the emission intensity for the blank terbium chloride medium is relatively low in FIG. 2.

FIG. 2 demonstrates the effectiveness of the invented detection method in detecting endospore presence. Both the filtered and unfiltered sample media exhibit peak emission intensities at the distinctive wavelengths of the terbium dipicolinate solution. Also, the peak emission intensities of the sample media are well above that of the blank medium. The invented methods are thus highly effective in indicating the presence of endospores in a sample medium of unknown endospore content.

EXAMPLE 2

Figure 3:
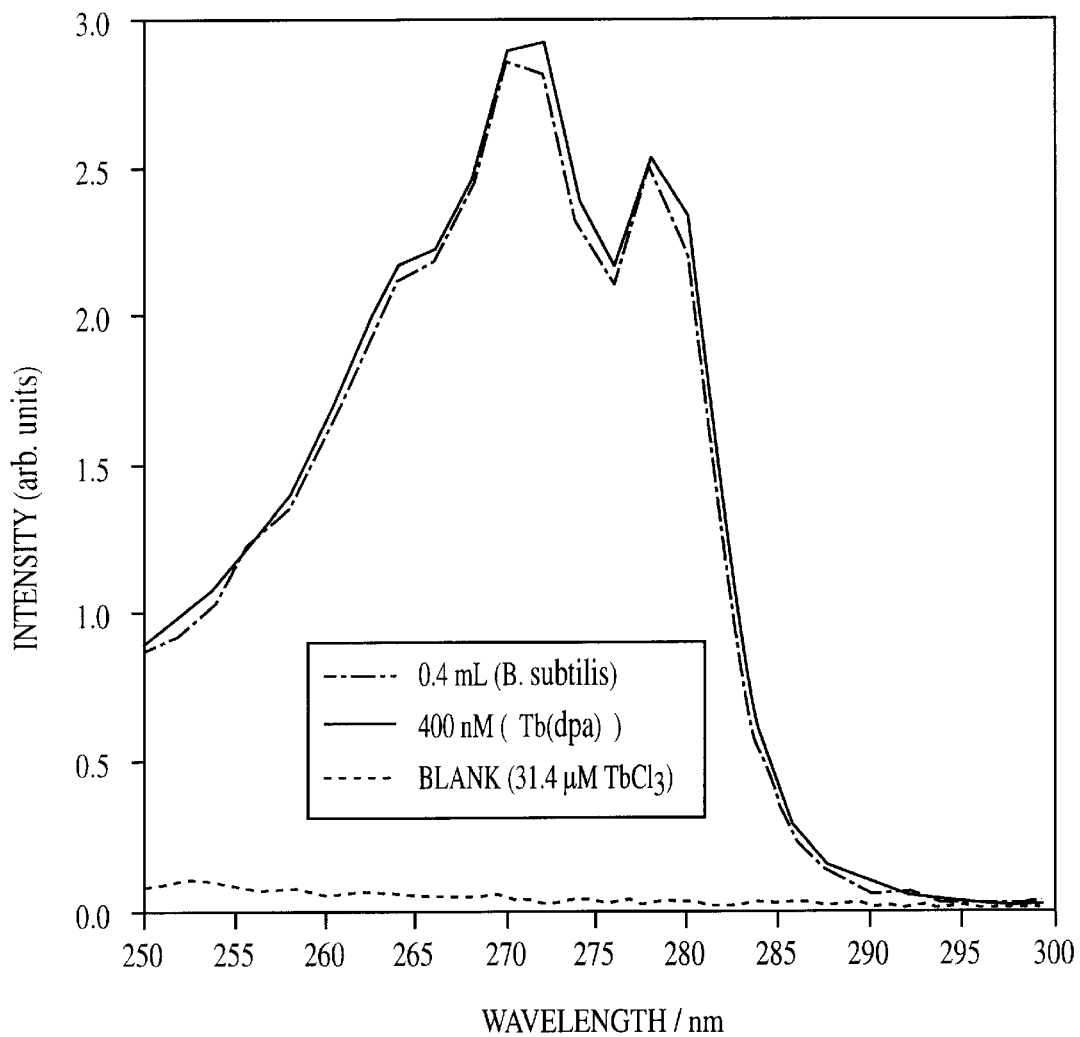
FIG. 3 is a graph of absorbance intensity versus wavelength for solutions of 400 nM terbium dipicolinate, 0.08 mL filtered an unfiltered *Bacillus subtilis* sample media, and a blank containing 200 $\mu$M of terbium chloride.

Referring to FIG. 3, the absorbance intensities for a sample medium with a 0.4 mL stock suspension of *Bacillus subtilis* combined with 31.4 $\mu$M terbium chloride, 400 nM of terbium dipicolinate and a blank medium with 31.4 $\mu$M terbium chloride solution are shown. The absorbance intensity of the sample medium mirrors that of the terbium dipicolinate, thus indicating that the terbium reacts with calcium dipicolinate present in the endospores. The blank medium absorption spectrum indicates the threshold level corresponding to the limit of detection. The excitation peaks in the sample medium occur at about 270 and 278 nm, as is expected for terbium dipicolinate. Preferably, in the invented method as applied to using terbium as the lanthanide, photoluminescence testing is performed with an excitation wavelength of 270 or 278 nm.

Figure 4:
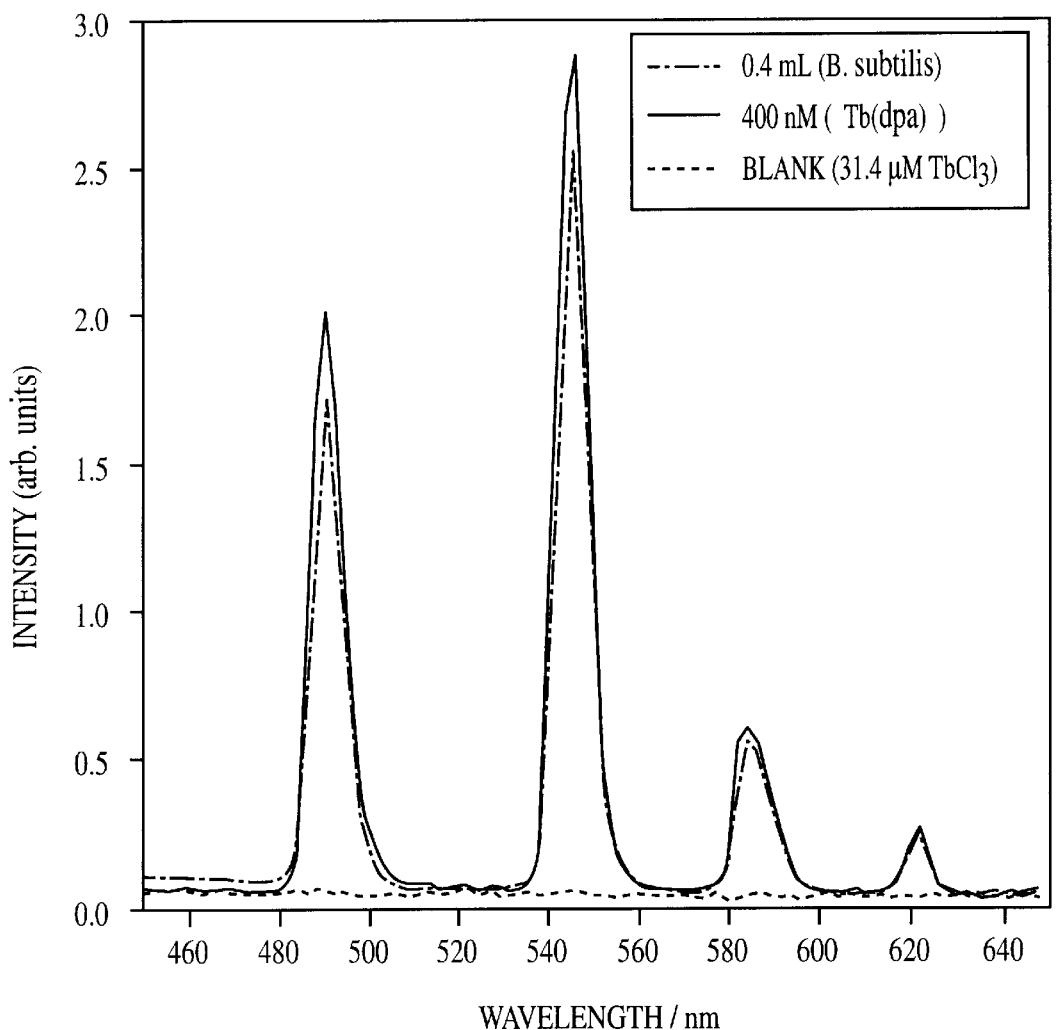
FIG. 4 is a graph of emission intensity versus wavelength for solutions of 50 nM terbium dipicolinate, 0.08 mL filtered an unfiltered *Bacillus subtilis* samples, and a blank containing 200 $\mu$M of terbium chloride.

In FIG. 4, the emission spectra for the same media indicated in FIG. 3 are shown for an excitation wavelength of 270 nm. As expected, the emission spectra of the combined terbium chloride-sample medium closely matches that of terbium dipicolinate, with emission peaks at 490 nm, 546 nm, 586 nm and 622 nm. The blank terbium chloride medium establishes a threshold level for the limit of detection. Emission intensities above this threshold level at the distinctive emission wavelengths of terbium dipicolinate thus reveals the presence of endospores in a sample medium of unknown endospore content.

Figure 5:
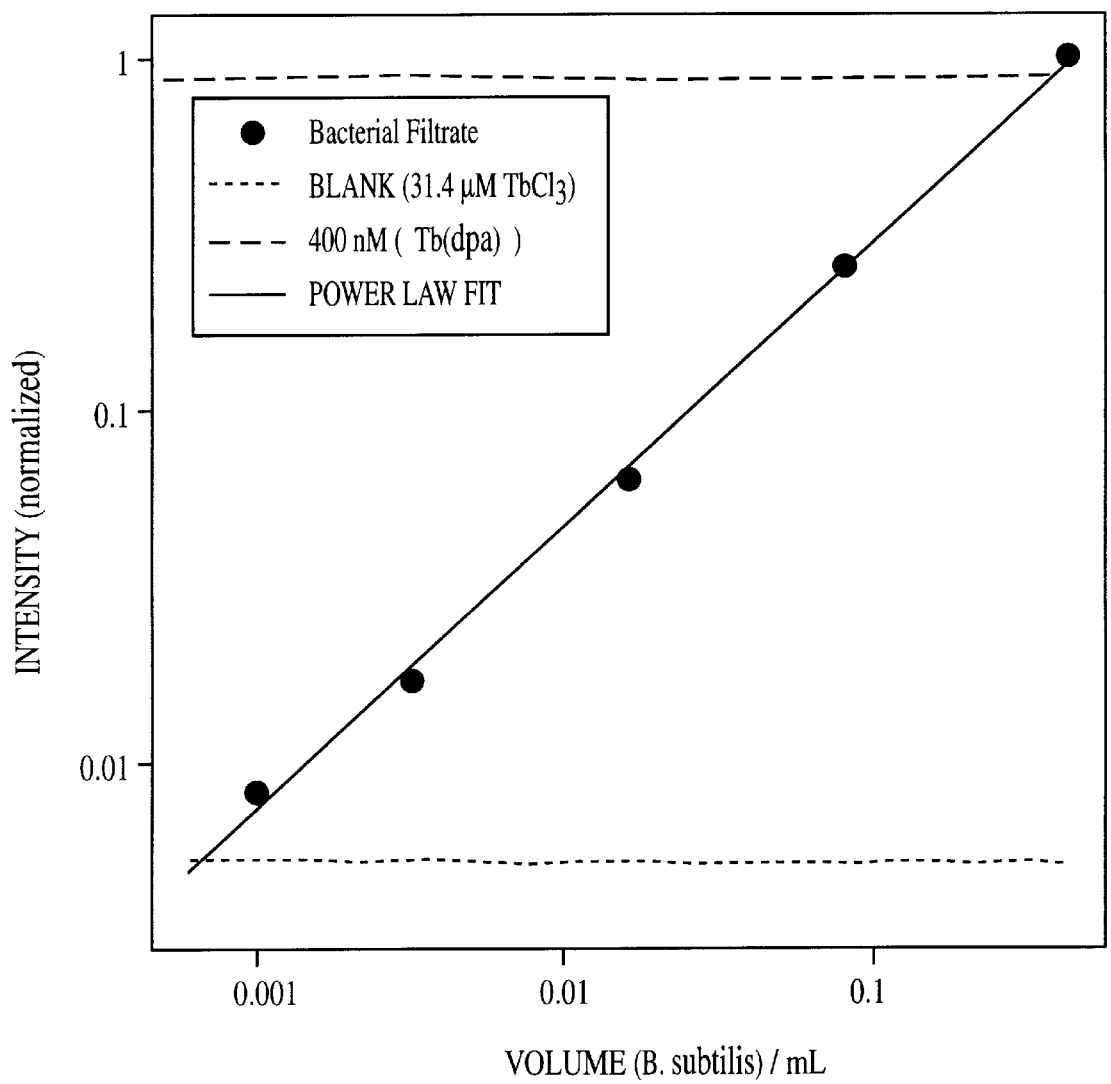
FIG. 5 is a graph of normalized emission intensity versus bacterial endospore concentration for use as a calibration curve in the quantification method to determine endospore concentration.

In the invented endospore quantification method, a calibration curve is prepared to relate the emission intensity of a sample medium with unknown endospore content at a distinctive lanthanide chelate emission wavelength, to the endospore concentration. Referring to FIG. 5, test sample media were prepared by combining stock spore suspensions of 0.0010, 0.0032, 0.0160, 0.080 and 0.40 mL with 31.4 $\mu$M terbium chloride solutions. The test sample media were excited at a wavelength of 270 nm, and the corresponding emission intensities at 546 nm were detected, normalized with the emission intensity of the 0.40 mL sample medium, and plotted on a log-log scale. Emission intensities were also plotted for 400 nM terbium dipicolinate and a blank medium with 31.4 $\mu$M terbium chloride. A power law fit of the five plots for each of the five sample media was used to prepare the calibration curve indicating the relationship between emission intensity and volume of the stock endospore suspension. The relationship of emission intensity to volume of stock spore suspension is nearly linear with a power law exponent of 0.80.

To use the calibration curve to determine endospore concentration in a sample medium of unknown endospore concentration, the unknown sample medium is prepared and subjected to photoluminescence testing under the same conditions used to determine the emission intensities of the five test media. Specifically, the unknown sample medium is combined with 31.4 $\mu$M terbium chloride and excited at an excitation wavelength of 270 nm. The resulting emission intensity at 546 nm is determined for the sample medium with unknown endospore content. Using the calibration curve, the stock endospore volume that corresponds to the emission intensity detected for the unknown sample medium is determined. Because the concentration of endospores per volume is known ($6.2 \times 10^9$ CFU/mL in this case), the endospore concentration for the sample medium with unknown endospore content can be readily determined.

In the above plot, five test sample media were used to prepare the calibration curve. Fewer or more test sample media may be desirable in a particular application, depending upon the desired accuracy.

The invented methods can be varied from the specific embodiments disclosed herein within the scope of this invention. For example, although photoluminescence testing is preferred for practice of the invented methods, there are other alternatives that can be used effectively. For example, electroluminescence could be used to determine absorbance or emission intensities for a sample medium.

The many features and advantages of the present invention are apparent from the detailed specification and thus, it is intended by the appended claims to cover all such features and advantages of the described methods which follow in the true spirit and scope of the invention. Further, since numerous modifications and changes will readily occur to those of ordinary skill in the art, it is not desired to limit the invention to the exact construction and operation illustrated and described. Accordingly, all suitable modifications and equivalents may be resorted to as falling within the spirit and scope of the invention.

I claim:

1. A method for detecting bacterial endospores in a medium, the method comprising the steps of:
   a) combining a lanthanide with a medium to be analyzed for bacterial endospore content, the lanthanide reacting with the bacterial endospores if present in the medium to form a lanthanide chelate;
   b) exciting any lanthanide chelate formed in said step (a) with an excitation energy distinctive of the lanthanide chelate;
   c) sensing whether emission occurs at an emission wavelength distinctive of the lanthanide chelate as a result of the excitation in said step (b); and
   d) determining whether bacterial endospores are present in the medium, based on said step (c).

2. The method as claimed in claim 1, wherein the lanthanide comprises terbium cations.

3. The method as claimed in claim 1, wherein the lanthanide comprises europium cations.

4. The method as claimed in claim 1, wherein the lanthanide is combined with the medium in an amount less than one molar.

5. The method as claimed in claim 1, wherein the medium includes a buffer.

6. The method as claimed in claim 1, wherein the lanthanide chelate comprises terbium dipicolinate.

7. The method as claimed in claim 1, wherein the lanthanide chelate comprises europium dipicolinate.

8. The method as claimed in claim 1, wherein, in said step (a), the lanthanide replaces calcium in calcium dipicolinate that is present in any bacterial endospores existing in the medium, to form the lanthanide chelate.

9. The method as claimed in claim 1, further comprising the step of:
   e) filtering the medium to separate insolubles including any bacterial endospores that may be present, from solubles including the lanthanide dissolved in the medium,
   said step (e) being performed after said step (a) but before said step (b).

10. The method as claimed in claim 1, wherein the lanthanide chelate is terbium dipicolinate and the exciting of said step (b) is performed with intense light having a wavelength in at least one of the ranges of 270±5 nanometers and 278±5 nanometers.

11. The method as claimed in claim 1, wherein the lanthanide chelate is terbium dipicolinate and the distinctive emission wavelength observed for the determination of said step (c) is in at least one of the ranges of 490±10 nanometers, 546±10 nanometers, 586±10 nanometers and 622±10 nanometers.

12. The method as claimed in claim 1, wherein said step (c) includes a substep of optically filtering the light emitted by the medium in said step (c) to eliminate light with wavelengths shorter than the distinctive emission wavelength of the lanthanide chelate.

13. The method as claimed in claim 1, wherein said steps (b) and (c) are performed with a spectrofluorometer.

14. The method as claimed in claim 1, further comprising the steps of:
   e) exciting a blank medium that contains no lanthanide chelate with substantially the same excitation energy used in said step (b);
   f) sensing an intensity level for emission from the blank medium caused by the excitation of said step (e), at substantially the same emission wavelength used for the determination in said step (c); and
   the determination in said step (d) concluding that bacterial endospores are present if the intensity level of the emission determined in said step (c) significantly exceeds the intensity level for the blank medium, and concluding that bacterial endospores are not present if the intensity level of the emission in said step (c) does not significantly exceed the intensity level for the blank medium.

15. The method as claimed in claim 1, wherein said steps (c) and (f) include respective substeps of optically filtering the light emitted by the medium in said steps (c) and (f) to eliminate light with wavelengths shorter than the distinctive emission wavelength of the lanthanide chelate.

16. The method as claimed in claim 1, wherein said step (b) is performed for a predetermined time period, and said step (c) is performed after a predetermined time delay from the end of the time period to allow background luminescence to subside before sensing the relatively long-lived luminescence of the lanthanide chelate.

17. The method as claimed in claim 16, wherein the lanthanide chelate includes at least one of terbium dipicolinate and europium dipicolinate.

18. A method for determining the concentration of bacterial endospores present in a medium, the method comprising the steps of:
   (a) combining a lanthanide with a medium to be analyzed for bacterial endospore content, the lanthanide reacting with the bacterial endospores if present in the medium to form a lanthanide chelate;
   (b) exciting any lanthanide chelate formed in said step (a) with an excitation energy distinctive of the lanthanide chelate;
   (c) determining the emission intensity that results from the excitation in said step (b) at an emission wavelength distinctive of the lanthanide chelate; and
   (d) determining the concentration of bacterial endospores present in the medium, based on said step (c).

19. The method as claimed in claim 18, wherein the lanthanide comprises terbium cation.

20. The method as claimed in claim 18, wherein the lanthanide comprises europium cation.

21. The method as claimed in claim 18, wherein the lanthanide is combined with the medium in an amount less than one molar.

22. The method as claimed in claim 18, wherein the medium includes a buffer.

23. The method as claimed in claim 18, wherein the lanthanide chelate comprises terbium dipicolinate.

24. The method as claimed in claim 18, wherein the lanthanide chelate comprises europium dipicolinate.

25. The method as claimed in claim 18, wherein in said step (a) the lanthanide replaces calcium in calcium dipicolinate that is present in any bacterial endospores existing in the medium, to form the lanthanide chelate.

26. The method as claimed in claim 18, further comprising the step of:
   e) filtering the medium to separate insolubles including any bacterial endospores that may be present, from solubles including the lanthanide dissolved in the medium,
   said step (e) being performed after said step (a) but before said step (b).

27. The method as claimed in claim 18, wherein the lanthanide chelate is terbium dipicolinate and the exciting of said step (b) is performed with intense light having a wavelength in at least one of the ranges of 270±5 nanometers and 278±5 nanometers.

28. The method as claimed in claim 18, wherein the lanthanide chelate is terbium dipicolinate and the distinctive emission wavelength observed for the determination of said step (c) is in at least one of the ranges of 490±10 nanometers, 546±10 nanometers, 586±10 nanometers and 622±10 nanometers.

29. The method as claimed in claim 18, wherein said step (c) includes a substep of optically filtering the light emitted by the medium in said step (c) to attenuate light with wavelengths shorter than the distinctive emission wavelength of the lanthanide chelate.

30. The method as claimed in claim 18, wherein said steps (b) and (c) are performed with a spectrofluorometer.

31. The method as claimed in claim 18, further comprising the steps of:

e) combining the lanthanide with a first predetermined concentration of bacterial endospores in a second medium to form lanthanide chelate;

f) exciting the second medium with the excitation energy used in said step (b);

g) determining the emission intensity of the second medium that results from the excitation of said step (f);

h) combining the lanthanide with a second predetermined concentration of bacterial endospores in a third medium to form lanthanide chelate;

i) exciting the third medium with the excitation energy used in said step (b);

j) determining the emission intensity of the third medium that results from the excitation of said step (i);

k) determining a calibration curve that relates emission intensity of the lanthanide chelate to bacterial endospore concentration, the determination of the bacterial endospore concentration in said step (d) being determined by relating the emission intensity determined in said step (c) to the bacterial endospore concentration existing in the medium tested in said steps (a)–(c) using the calibration curve.

32. The method as claimed in claim 31, wherein at least one of said steps (c), (g) and (j) include respective substeps of optically filtering the light emitted by the medium to eliminate light with wavelengths shorter than the distinctive emission wavelength of the lanthanide chelate.

33. The method as claimed in claim 31, wherein the medium tested in said steps (a)–(c) and the second and third media are substantially the same in lanthanide molarity and buffer content except for the respective bacterial endospore concentrations.

34. The method as claimed in claim 18, wherein said step (b) is performed for a predetermined time period, and said step (c) is performed after a predetermined time delay from the end of the time period to allow background luminescence to subside before sensing whether the relatively long-lived luminescence of the lanthanide chelate is present.

35. A method for detecting bacterial endospores in a medium, the method comprising the steps of:

(a) combining a lanthanide with a sample medium; and (b) determining whether the combined lanthanide and sample medium includes a lanthanide chelate indicative of the presence of bacterial endospores.

36. The method as claimed in claim 35, wherein said step (b) is performed using photoluminescence testing of any lanthanide chelate that results from the performance of said step (a).

37. The method as claimed in claim 35, wherein said step (b) is performed by exciting the sample medium and determining whether significant absorption occurs at wavelengths distinctive of the lanthanide chelate.

38. The method as claimed in claim 35, wherein said step (b) is performed by exciting the sample medium and determining whether significant emission occurs at wavelengths distinctive of the lanthanide chelate.

39. The method as claimed in claim 35, wherein said step (b) is performed by exciting the sample medium for a predetermined time period, and said step (c) is performed after a predetermined time delay sufficient to allow background luminescence to subside.

40. A method for determining the concentration of bacterial endospores present in a medium, the method comprising the steps of:

(a) combining a lanthanide with a sample medium; and (b) determining the concentration of bacterial endospores present in the combined lanthanide and sample medium, based on the amount of lanthanide chelate resulting from the combination of lanthanide with the sample medium in said step (a).

41. The method as claimed in claim 40, wherein said step (b) is performed using photoluminescence testing of the lanthanide chelate.

42. The method as claimed in claim 41, wherein said step (b) includes the substeps of b1) preparing a calibration curve that relates the absorbance intensity to the endospore concentration using photoluminescence testing of at least two test sample media having different predetermined endospore concentrations;

b2) performing the photoluminescence testing on the sample medium with unknown endospore content to determine an absorbance intensity for the unknown sample medium; and b3) relating the absorbance intensity for the unknown sample medium to an endospore concentration, using the calibration curve.

43. The method as claimed in claim 41, wherein said step (b) includes the substeps of b1) preparing a calibration curve that relates emission intensity to the endospore concentration using photoluminescence testing of at least two test sample media having different predetermined endospore concentrations;

b2) performing the photoluminescence testing on the sample medium with unknown endospore content to determine an emission intensity for the unknown sample medium; and b3) relating the emission intensity for the unknown sample medium to an endospore concentration, using the calibration curve.

* * * * *